United States Patent [19]

Blaha et al.

[11] Patent Number: 4,568,158
[45] Date of Patent: Feb. 4, 1986

[54] BINOCULAR OPHTHALMOSCOPE

[75] Inventors: Erich Blaha, Esslingen; Roland Trentin, Aalen, both of Fed. Rep. of Germany

[73] Assignee: Carl-Zeiss-Stiftung, Heidenheim on the Brenz, Fed. Rep. of Germany

[21] Appl. No.: 593,711

[22] Filed: Mar. 26, 1984

[30] Foreign Application Priority Data

Apr. 2, 1983 [DE] Fed. Rep. of Germany ....... 3312086

[51] Int. Cl.$^4$ .......................... A61B 3/10; G02B 27/02
[52] U.S. Cl. ..................................... 351/205; 350/145
[58] Field of Search ............... 351/205, 211, 221, 214, 351/206; 350/145

[56] References Cited

U.S. PATENT DOCUMENTS

| 2,757,574 | 8/1956 | Thorburn | 350/145 |
| 3,582,191 | 6/1971 | Cohen et al. | 350/205 |
| 3,963,329 | 6/1976 | Stumpf et al. | 351/205 |

Primary Examiner—Rodney B. Bovernick
Assistant Examiner—Paul Dzierzynski
Attorney, Agent, or Firm—Stonebraker, Shepard & Stephens

[57] ABSTRACT

A binocular ophthalmoscope having two horizontally displaceable deflecting mirrors in the ray paths from the two eyes of the observer to the pupil of the eye being examined, and a vertically displaceable and also tiltable mirror in the beam path from a source of illumination to the pupil of the eye being examined. Movement of the horizontally displaceable mirrors toward or away from each other varies the stereoscopic base of observation. Vertical displacement and tilting of the other mirror serves to vary the location where the illuminating beam enters the pupil relative to the location where the rays from the eyes of the observer enter the pupil of the eye being examined. The mechanism for vertically moving and tilting the third mirror is coupled to the mechanism for moving the two horizontally displaceable mirrors, enabling the adjustments to be performed from a single manually operable adjusting knob, more easily and conveniently than in prior arrangements where successive operation of two adjusting members may be required.

7 Claims, 4 Drawing Figures

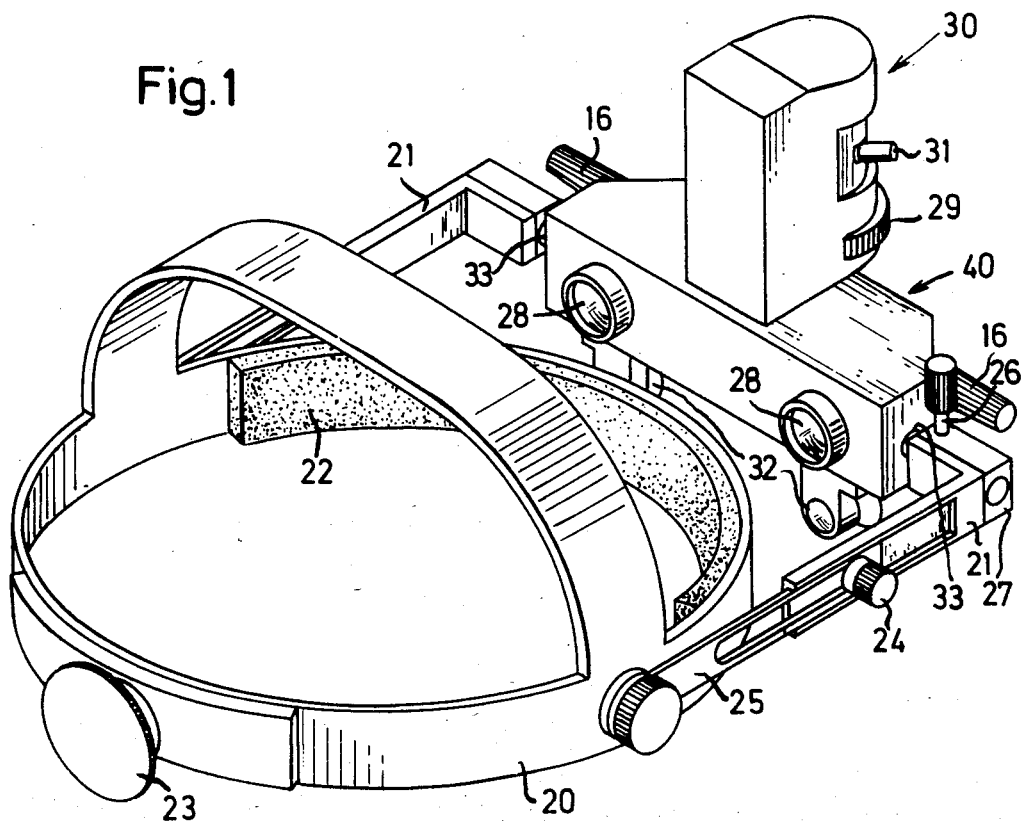
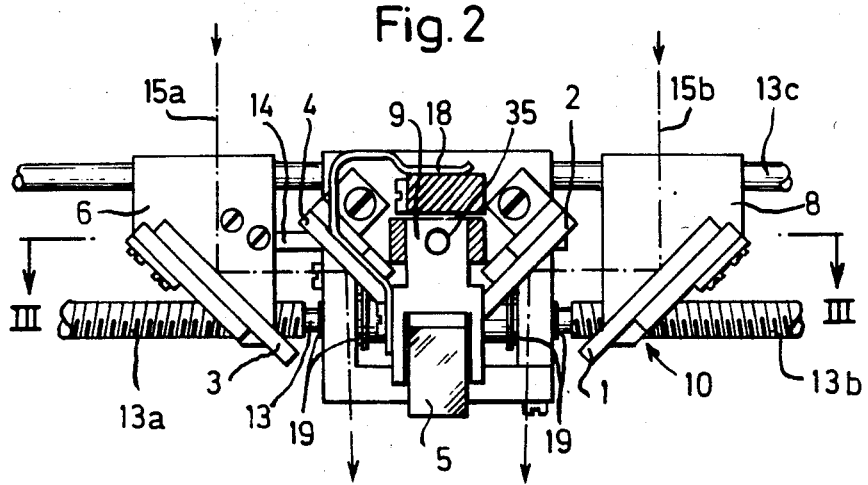

BINOCULAR OPHTHALMOSCOPE

This invention relates to a binocular ophthalmoscope having provision for projecting an observation light beam into the pupil of an eye of the person being examined, and for directing rays from both eyes of the examining person (e.g., an ophthalmologist) to the pupil of the eye being examined. The invention deals particularly with the easy, rapid, and convenient adjustment of the paths of the rays or beams, and is especially useful in those situations where the pupil of the person being examined can not be dialated and must remain relatively small during the examination.

In examinations with a binocular ophthalmoscope, the pupils of the observer and the observation light source are imaged in the pupil of the patient. For good stereoscopic viewing, these three images should be as far apart as possible in the pupil of the patient. Ordinarily the patient's pupil is dialated by medication to afford the observer maximum stereoscopic viewing. However, there are some patients whose pupils can not be dialated. In order to permit some degree of stereoscopic viewing even in the case of relatively small pupils while using one and the same instrument used for viewing normally dialated pupils, binocular ophthalmoscopes have been developed in which the images of the pupils of the observer and of the observation light source can be brought closer together by optical means.

One such ophthalmoscope is disclosed in German Federal Republic Patent No. 3,020,750 of Foerster, Aug. 19, 1982. In this patent, for examination of small pupils of patients two mirrors are displaced or adjusted by an operating knob. This changes the angle of convergence between the observation ray paths. By actuating a different knob, another mirror is moved, which changes the direction of the illumination ray path and thus changes the position of the image of the source of illumination.

The adjusting of the ophthalmoscope to the eye of the patient by successive actuation of two different adjusting knobs is a substantial drawback or disadvantage of this construction. It is, therefore, an object of the present invention to provide a binocular ophthalmoscope in which it is easier and more convenient to adjust the instrument to the eye of a patient having a small pupil.

This object is achieved, according to the invention, by the provision of mechanism for displacing or adjusting the position of mirrors controlling the path of rays from the eyes of the observer to the eye of the patient, coupled with mechanism for displacing and tilting a mirror which controls the beam from the illumination device to the eye of the patient, so that these adjustments may all be effected by manipulation of only a single adjusting knob.

The advantages obtained by the present invention reside particularly in the fact that the ability to make all the needed adjustments from a single adjusting knob shortens the time required for the adjustment and simplifies it and makes the adjustment more convenient for the user of the instrument, and also in the fact that, because only one knob is needed, it is possible and practical to provide such a knob on each side of the instrument, thus making adjustment equally convenient for both right-handed and left-handed users.

BRIEF DESCRIPTION OF THE DRAWINGS

An illustrative embodiment of the invention is shown in the accompanying drawings, in which:

FIG. 1 is a perspective view of a binocular ophthalmoscope according to a preferred embodiment of the invention;

FIG. 2 is a fragmentary view partly in plan and partly in horizontal section through the observation unit of the ophthalmoscope, the sectional portion of this view being taken approximately on the line II—II of FIG. 4;

DETAILED DESCRIPTION

Figure 3:
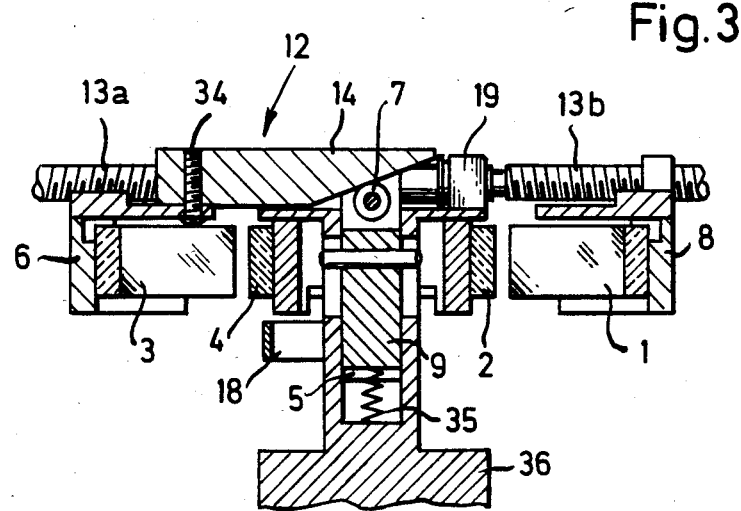
FIG. 3 is a fragmentary vertical section taken approximately on the line III—III of FIGS. 2 and 4.

Referring now to FIG. 1, the instrument is supported from suitable headgear including a forehead strap 20 encircling the head of the user, the strap having a soft cushioning layer 22. To fit heads of different sizes, the size of the circumference of the strap is adjustable, being held at the desired size by a clamping screw 23. Support arms extend forwardly from each side of the head strap, and the ophthalmoscope is mounted on the forward ends of these support arms. Each support arm has two elongated parts 21 and 25 longitudinally slidable telescopically relative to each other and clamped in any desired position by a clamping screw 24. This enables the instrument supported by the arms to be held at varying distances from the eyes of the observer wearing the headgear.

The ophthalmoscope includes an illuminating unit or portion indicated in general at 30, and an observation unit or portion indicated in general at 40. The details of the mounting of these units on the forward ends of the support arms may be varied widely without departing from the invention. Merely as one example of suitable mounting, the forward ends of the support arm portions 21 may engage bearing blocks 27 which serve as bearings for spindles 33 which project laterally from opposite sides of the observation unit 40. The support arms 21 may be adjusted laterally relative to these bearing blocks 27, in order to accommodate the apparatus to wider or narrower heads of wearers of the supporting headgear. Also, the spindles 33 may turn in the bearing blocks, to invert the ophthalmoscope body so that telescopes 32 mounted on the bottom of the body may be brought up into alignment with the eyes of the user or observer, for use in a different kind of ophthalmological examination. Suitable clamping screws, one of which is shown at 26, are provided for holding the parts in the desired positions.

The illuminating unit 30 has a knurled rotary disk 29 and a movable handle 31. By manipulating these, selected field diaphragms and filters may be inserted in the illumination ray path. Except for the mechanism described below for adjusting the mirror which controls the direction and location of the illumination ray, the construction of the illuminating unit may be conventional.

The observation unit 40 has two eyepieces 28 aligned with the eyes of the observer, through which the observer views the pupil of the eye of the patient being examined. Referring now to FIG. 2, the ray paths from the eyes of the observer to the eye of the patient are indicated by dot-dash lines 15a (from the right eye of the observer) and 15b (from the left eye).

The ray path 15b from the left eye (i.e., the right-hand ray path when viewed from the front as in FIG. 2) proceeds forwardly until it is deflected laterally by the movable mirror 1 to the fixed mirror 2, where it is deflected forwardly again toward the pupil of the patient's eye being examined. Similarly, the ray path 15a from the right eye of the observer goes forwardly to the movable mirror 3, is there deflected laterally to the fixed mirror 4, and then goes forwardly again to the eye being examined. Moving the mirrors 1 and 3 closer to or farther away from each other alters the stereoscopic base of the observation ray paths.

To enable such movement, the mirrors 1 and 3 are mounted on separate supports or carriers 8 and 6, respectively, which slide along a guide rail in the form of a fixed shaft 13c. Portions of these mirror supports 8 and 6 engage threads on a threaded spindle 13 which has bearings 19 in fixed parts of the observation unit 40. The spindle 13 has left-handed threads 13a which engage the support 6 of the mirror 3 and right-handed threads 13b which engage the support 8 of the mirror 1. Both ends of the spindle 13 project laterally beyond the sides of the housing of the observation unit 40. The projecting ends of the spindle are provided with accessible operating knobs 16, so that the spindle may be conveniently turned by either a right-handed user or a left-handed user of this equipment. Turning the spindle in one direction will move the mirrors 1 and 3 closer to each other, reducing the stereoscopic base of observation, while turning in the opposite direction will move these mirrors farther apart, increasing the stereoscopic base.

The illumination beam comes vertically downwardly from the illuminating unit 30 until it striked the mirror 5 (see especially FIGS. 2 and 4) which deflects this beam forwardly to the eye being examined. This mirror 5 is mounted both for upward and downward adjusting movement and for tilting movement. According to the present invention, both of these movements of the mirror 5 are performed from the same adjusting knob 16 which is used to adjust the mirrors 1 and 3.

For the upward and downward displacement of the mirror 5, there is means indicated in general at 12, comprising a wedge 14 fastened by a screw 34 (FIG. 3) to the support 6 of the mirror 3, so that the wedge travels with the support 6. This wedge constitutes a cam which engages and displaces a cam-follower in the form of a roller 7, rotatable on a pin fixed in the support or carrier 9 of the illumination beam mirror 5. As seen in FIG. 3, this support 9 is mounted to slide vertically in guideways in a fixed part of the structure 36 which constitutes part of the main frame of both the illuminating unit 30 and the observation unit 40. When the mirror 3, support 6, and wedge or cam 14 move in one direction (rightwardly when viewed as in FIG. 3), the roller 7 will ride up the incline of the wedge, moving the carrier 9 of the mirror 5 upwardly in its guideways, against the force of the spring 35. When the wedge moves in the opposite direction, the spring 35 will push the carrier 9 and mirror 5 downwardly, keeping the roller 7 in contact with the cam surface of the wedge.

Figure 4:
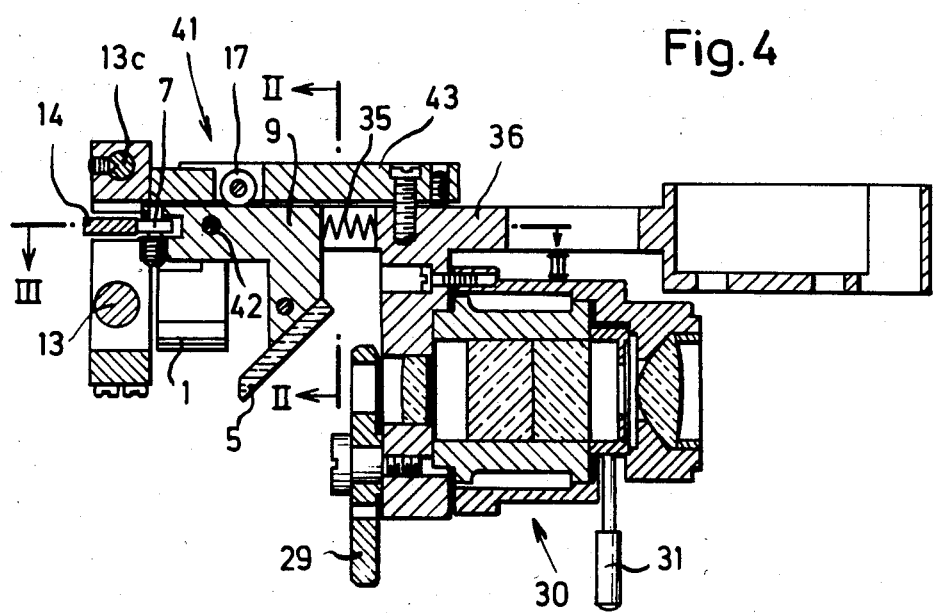
FIG. 4 is a fragmentary vertical section taken centrally through the apparatus along a section plane at right angles to the plane of FIG. 3.

For causing the desired tilting of the mirror 5 in addition to its upward and downward displacement, there is tilting means indicated in general at 41 in FIG. 4. The support or carrier 9 of the mirror 5 is mounted for limited tilting movement on the pin 42 (FIG. 4), the ends of which extend into and travel up and down slots which constitute guideways in the fixed part 36, as seen in FIG. 3. A roller 17 (FIG. 4) presses against the rear face of the support 9, i.e., the face which is toward the observer and away from the patient. This roller 17 is mounted in a mounting block or bearing block 43 which is fastened to the stationary part 36 by adjusting screws in such a way as to enable a fine adjustment of the exact position of the block and its roller 17, to determine exactly the desired degree of tilt caued to the mirror carrier 9 by the pressure of the roller 17. Moreover, as the mirror support 9 moves upwardly and downwardly by action of the wedge or cam 14 (and spring 35), the degree of tilt will change as the pivot 42 moves closer to or farther away from the roller 17. Also the degree of tilt may be caused to change by giving an appropriate cam-like shape to that portion of the surfae of the support 9 on which the roller 17 rides when the support moves. A spring 18 (FIGS. 2 and 3) keeps the support 9 pressed against the roller 17.

With this combination of upward and downward motion of the mirror 5 and tilting motion of the mirror, the illuminating beam projected from the illuminating device or unit 30 to the eye being examined may be controlled to exactly the position and inclination desired, and the angle between the illumination ray path and the plane of observation may be changed as necessary.

With the present invention, all of these adjustments are performed by manual operation of a single knob or adjusting member. It is not necessary to operate two separate knobs in succession. The shape of the wedge and the dimensions of all of the cooperating parts are so designed and correlated that just the desired degree of displacement and tilt of the mirror 5 is accomplished for a given movement of the observation mirrors 1 and 3 toward or away from each other. In FIG. 2, the numeral 10 is intended to indicate in general the means for horizontal displacement of the mirrors 1 and 3.

It is possible to make the angle of the wedge variable, so that upon a given change in the stereo base (by horizontal displacement of the mirrors 1 and 3) a vertical displacement of the mirror 5 results.

It is also possible to make the distance between the pivot point 42 and the point of contact of the roller 17 adjustable, whereby upon vertical displacement of the mirror 5, the inclination or tilting thereof takes place. Upon horizontal displacement of the support 6, the wedge 14 is moved relative to the roller 7 and thereby puts the support 9 in vertical movement.

What is claimed is:

1. A binocular ophthalmoscope comprising an observation unit and an illuminating unit connected with each other, said units including adjusting means for adjusting the position of images of pupils of eyes of an observer in the pupil of an eye being examined and adjusting the position of an image of a source of illumination also in the pupil of the eye being examined, said adjusting means including a stationary mirror (2, 4) and a laterally displaceable mirror (1, 3) in each ray path from an eye of the observer to the eye being examined and a displaceable mirror (5) in a beam path from said illuminating unit to said eye being examined, first displacing means (10) for displacing at least one of said laterally displaceable mirrors (1, 3), second displacing means (12) for displacing said beam path mirror (5), said first and second displacing means being coupled together for conjoint movement, and single operating means (16) for operating both of said displacing means concomitantly.

2. The invention defined in claim 1, wherein said beam path mirror (5) is mounted for straight-line displacement and also for tilting movement and wherein said second displacing means (12) performs straight-line displacement, further comprising third displacing means (41) for performing tilting movement of said mirror (5) concomitantly with and as a result of displacement of said mirror by said second displacing means.

3. The invention defined in claim 1, wherein said observation unit includes a housing and a support for said illuminating unit, and wherein said adjusting means includes a spindle (13) passing through said housing from side to side and supported in its central region from said support, said spindle having threaded portions with respective left-hand and right-hand threads (13a, 13b) operatively connected to respective mirror supports (6, 8) which respectively support said laterally displaceable mirrors (3, 1) whereby rotation of said spindle in one direction will cause said mirrors to be moved toward each other and rotation in the opposite direction will cause said mirrors to be moved away from each other, further comprising a third mirror support (9) supporting said beam path mirror (5), a cam (14) operatively connected to and moving with the support (6) of one of said horizontally displaceable mirrors (3), said cam acting on said third mirror support (9) to cause vertical displacement thereof.

4. The invention defined in claim 3, further comprising a roller (17) acting on said third mirror support (9) to cause tilting of said support (9) and the mirror (5) carried thereby as said third mirror support is displaced vertically by action of said cam (14).

5. The invention defined in claim 3, wherein said spindle (13) carries an operating knob (16) at each end thereof in an accessible position externally of said housing, for optional actuation by a right-handed or left-handed user.

6. A binocular ophthalmoscope comprising first optical means for defining ray paths from both eyes of an observer toward a pupil of an eye of a patient being examined, second optical means for defining a beam path from a source of illumination toward said pupil, first adjusting means for adjusting said first optical means to vary a stereoscopic base of observation, second adjusting means for adjusting said second optical means to vary the location where said beam path enters said pupil relative to the location where said ray paths from the eyes of the observer enter said pupil, means coupling said first adjusting means and said second adjusting means for conjoint movement, and a single manually operated adjusting member for concomitantly operating both said first adjusting means and said second adjusting means together.

7. The invention defined in claim 6, wherein said single manually operated adjusting member is a laterally extending shaft with opersating knobs on both ends for easy operation by both right-handed and left-handed observers using the ophthalmoscope.

* * * * *